(12) United States Patent
Guck et al.

(10) Patent No.: US 6,564,106 B2
(45) Date of Patent: May 13, 2003

(54) THIN FILM ELECTRODES FOR SENSING CARDIAC DEPOLARIZATION SIGNALS

(75) Inventors: Beth Anne Guck, Blaine, MN (US); Adrianus P. Donders, Founex (CH)

(73) Assignee: Medtronic, Inc., Minneapolis, MN (US)

(*) Notice: Subject to any disclaimer, the term of this patent is extended or adjusted under 35 U.S.C. 154(b) by 252 days.

(21) Appl. No.: 09/736,046

(22) Filed: Dec. 13, 2000

(65) Prior Publication Data

US 2002/0072778 A1 Jun. 13, 2002

(51) Int. Cl.$^7$ ................................. A61N 1/00
(52) U.S. Cl. .............. 607/116; 607/119; 607/122; 600/373; 600/374
(58) Field of Search ............... 607/116, 119, 607/129, 142, 9, 32, 122, 36, 4; 600/373, 374, 375

(56) References Cited

U.S. PATENT DOCUMENTS

| | | | |
|---|---|---|---|
| 3,983,867 A | 10/1976 | Case | 128/2.06 |
| 4,023,565 A | 5/1977 | Ohlsson | 128/2.06 B |
| 4,082,086 A | 4/1978 | Page et al. | 128/2.06 E |
| 4,121,576 A | 10/1978 | Greensite | 128/2.06 V |
| 4,170,227 A | 10/1979 | Feldman et al. | 128/704 |
| 4,263,919 A | 4/1981 | Levin | 128/708 |
| 4,310,000 A | 1/1982 | Lindemans | 128/419 PG |
| 4,313,443 A | 2/1982 | Lund | 128/642 |
| 4,476,868 A | 10/1984 | Thompson | 128/419 PG |
| 4,593,702 A | 6/1986 | Kepski et al. | 128/696 |
| 4,674,508 A | 6/1987 | DeCote | 128/419 PT |
| 4,729,376 A | 3/1988 | DeCote, Jr. | 128/419 PT |
| 5,052,388 A | 10/1991 | Sivula et al. | 128/419 PG |
| 5,331,966 A | 7/1994 | Bennett et al. | 128/696 |
| 5,345,362 A | 9/1994 | Winkler | 361/681 |
| 5,480,416 A | 1/1996 | Garcia et al. | 607/36 |
| 5,749,911 A | 5/1998 | Westlund | 607/36 |

FOREIGN PATENT DOCUMENTS

FR  2 559 671  2/1984  ........ A61N/1/362

OTHER PUBLICATIONS

09/696,365 "Multilayer Ceramic Electrode for Sensing Cardiac Depolarization Signals" filed Oct. 25, 2000.
09/697,438 "Surround Shroud Connector and Electrode Housings for a Subcutaneous Electrode Array and Leadless ECGS" filed Oct. 26, 2000.
09/703,152 "Subcutaneous Spiral Electrode for Sensing Electrical Signals of the Heart" filed Oct. 31, 2000.

*Primary Examiner*—Teresa Walberg
*Assistant Examiner*—Fadi H. Dahbour
(74) *Attorney, Agent, or Firm*—Girma Wolde-Michael

(57) ABSTRACT

A subcutaneous electrode is structured to acquire electrocardiographic data and waveform tracings from an implanted pacemaker without the need for or use of surface (skin) electrodes. Thin film electrodes disposed on a top surface of a feedthrough are adapted to connect into an assembly at the peripheral edge of the implantable device. Each of the electrodes comprise an integral element of a subcutaneous electrode array or SEA which detects cardiac depolarizations that are communicable and displayable by a portable device programmer. The thin film electrode is a complete functional component with a hermetically attached weld ring adapted for direct welding into the implanted device casing. The distribution and dispersion of the electrodes around the perimeter of the pacemaker provide a maximum and equidistance setting of electrode pairs for either three or four preferred electrode configurations.

15 Claims, 8 Drawing Sheets

THIN FILM ELECTRODES FOR SENSING CARDIAC DEPOLARIZATION SIGNALS

FIELD OF THE INVENTION

The present invention relates generally to implantable pacemakers and particularly to a subcutaneous electrode used to sense, record, and acquire electrocardiographic data and waveform tracings from an implanted pacemaker without the need for or use of surface (skin) electrodes. More particularly, the present invention relates to thin film electrodes placed onto a modified top surface of a feedthrough fitting into an assembly incorporated along and into the peripheral edge of the implantable pacemaker. Each thin film electrode becomes an integral element of a Subcutaneous Electrode Array or SEA that, in turn, detects cardiac depolarizations communicable and displayable by a portable device programmer.

BACKGROUND OF THE INVENTION

The electrocardiogram (ECG) is commonly used in medicine to determine the status of the electrical conduction system of the human heart. As practiced, an ECG recording device is commonly attached to the patient via ECG leads connected to pads arrayed on the patient's body so as to achieve a recording that displays the cardiac waveforms in any one of 12 possible vectors.

Since the implantation of the first cardiac pacemaker, implantable medical device technology has advanced with the development of sophisticated, programmable cardiac pacemakers, pacemaker-cardioverter-defibrillator arrhythmia control devices and drug administration devices designed to detect arrhythmias and apply appropriate therapies. The detection and discrimination between various arrhythmic episodes in order to trigger the delivery of an appropriate therapy is of considerable interest. Prescription for implantation and programming of the implanted device are based on the analysis of the PQRST electrocardiogram (ECG) and the electrogram (EGM). The waveforms are usually separated for such analysis into the P-wave and R-wave in systems that are designed to detect the depolarization of the atrium and ventricle respectively. Such systems employ detection of the occurrence of the P-wave and R-wave, analysis of the rate, regularity, and onset of variations in the rate of recurrence of the P-wave and R-wave, the morphology of the P-wave and R-wave and the direction of propagation of the depolarization represented by the P-wave and R-wave in the heart. The detection, analysis and storage of such EGM data within implanted medical devices are well known in the art. Acquisition and use of ECG tracing (s), on the other hand, has generally been limited to the use of an external ECG recording machine attached to the patient via surface electrodes of one sort or another.

The aforementioned ECG systems that utilize detection and analysis of the PQRST complex are all dependent upon the spatial orientation and number of electrodes located on the body or placed near and around the heart to detect the depolarization wave front.

As the functional sophistication and complexity of implantable medical device systems increased over the years, it has become increasingly more important for such systems to include a system for facilitating communication between one implanted device and another implanted device and/or an external device, for example, a programming console, monitoring system, or the like. For diagnostic purposes, it is desirable that the implanted device be able to communicate information regarding the device's operational status and the patient's condition to the physician or clinician. State of the art implantable devices are available which can even transmit a digitized electrical signal to display electrical cardiac activity (e.g., an ECG, EGM, or the like) for storage and/or analysis by an external device. The surface ECG, however, has remained the standard diagnostic tool since the very beginning of pacing and remains so today.

To diagnose and measure cardiac events, the cardiologist has several tools from which to choose. Such tools include twelve-lead electrocardiograms, exercise stress electrocardiograms, Holter monitoring, radioisotope imaging, coronary angiography, myocardial biopsy, and blood serum enzyme tests. Of these, the twelve-lead electrocardiogram (ECG) is generally the first procedure used to determine cardiac status prior to implanting a pacing system; thereafter, the physician will normally use an ECG available through the programmer to check the pacemaker's efficacy after implantation. Such ECG tracings are placed into the patient's records and used for comparison to more recent tracings. It must be noted, however, that whenever an ECG recording is required (whether through a direct connection to an ECG recording device or to a pacemaker programmer), external electrodes and leads must be used.

Unfortunately, surface electrodes have some serious drawbacks. For example, electrocardiogram analysis performed using existing external or body surface ECG systems can be limited by mechanical problems and poor signal quality. Electrodes attached externally to the body are a major source of signal quality problems and analysis errors because of susceptibility to interference such as muscle noise, power line interference, high frequency communication equipment interference, and baseline shift from respiration. Signal degradation also occurs due to contact problems, ECG waveform artifacts, and patient discomfort. Externally attached electrodes are subject to motion artifacts from positional changes and the relative displacement between the skin and the electrodes. Furthermore, external electrodes require special skin preparation to ensure adequate electrical contact. Such preparation, along with positioning the electrode and attachment of the ECG lead to the electrode needlessly prolongs the pacemaker follow-up session. One possible approach is to equip the implanted pacemaker with the ability to detect cardiac signals and transform them into a tracing that is the same as or comparable to tracings obtainable via ECG leads attached to surface electrodes.

It is known in the art to monitor electrical activity of the human heart for diagnostic and related medical purposes. U.S. Pat. No. 4,023,565 issued to Ohlsson describes circuitry for recording ECG signals from multiple lead inputs. Similarly, U.S. Pat. No. 4,263,919 issued to Levin, U.S. Pat. No. 4,170,227 issued to Feldman, et al, and U.S. Pat. No. 4,593,702 issued to Kepski, et al, describe multiple electrode systems that combine surface EKG signals for artifact rejection.

The primary use for multiple electrode systems in the prior art appears to be vector cardiography from ECG signals taken from multiple chest and limb electrodes. This is a technique whereby the direction of depolarization of the heart is monitored, as well as the amplitude. U.S. Pat. No. 4,121,576 issued to Greensite discusses such a system.

Numerous body surface ECG monitoring electrode systems have been employed in the past in detecting the ECG and conducting vector cardiographic studies. For example, U.S. Pat. No. 4,082,086 issued to Page, et al., discloses a four electrode orthogonal array that may be applied to the patient's skin both for convenience and to ensure the precise orientation of one electrode to the other. U.S. Pat. No. 3,983,867 issued to Case describes a vector cardiography system employing ECG electrodes disposed on the patient in normal locations and a hex axial reference system orthogonal display for displaying ECG signals of voltage versus time generated across sampled bipolar electrode pairs.

U.S. Pat. No. 4,310,000 to Lindemans and U.S. Pat. Nos. 4,729,376 and 4,674,508 to DeCote, incorporated herein by reference, disclose the use of a separate passive sensing reference electrode mounted on the pacemaker connector block or otherwise insulated from the pacemaker case in order to provide a sensing reference electrode that is not part of the stimulation reference electrode and thus does not have residual after-potentials at its surface following delivery of a stimulation pulse.

Moreover, in regard to subcutaneously implanted EGM electrodes, the aforementioned Lindemans U.S. Pat. No. 4,310,000 discloses one or more reference sensing electrode positioned on the surface of the pacemaker case as described above. U.S. Pat. No. 4,313,443 issued to Lund describes a subcutaneously implanted electrode or electrodes for use in monitoring the ECG.

U.S. Pat. No. 5,331,966 to Bennett, incorporated herein by reference, discloses a method and apparatus for providing an enhanced capability of detecting and gathering electrical cardiac signals via an array of relatively closely spaced subcutaneous electrodes (located on the body of an implanted device).

More recently, patent application Ser. No. 09/697,438, filed Oct. 26, 2000, entitled Surround Shroud Connector and Electrode Housings for a Subcutaneous Electrode Array and Leadless ECGs, by Ceballos, et al., incorporated herein by reference in its totality, discloses an alternate method and apparatus for detecting electrical cardiac signals via an array of subcutaneous electrodes located on a shroud circumferentially placed on the perimeter of an implanted pacemaker. An associated submission, patent application Ser. No. 09/703,152, filed Oct. 31, 2000, entitled Subcutaneous Electrode for Sensing Electrical Signals of the Heart by Brabec et al, incorporated herein by reference in its totality, discloses the use of a spiral electrode using in conjunction with the shroud described in patent application Ser. No. 09/697, 438. In addition, patent application Ser. No. 09/696,365, filed Oct. 25, 2000, entitled Multilayer Ceramic Electrodes For Sensing Cardiac Depolarization Signals by Guck et al, also incorporated herein by reference in its totality, discloses the use of the aforementioned electrodes around the perimeter of an implanted pacemaker.

SUMMARY OF THE INVENTION

The present invention encompasses a Subcutaneous Thin Film Electrode that is applied to the uppermost surface of a feedthrough and placed into an assembly that is welded individually into three or four openings placed around the perimeter of an implantable pacemaker. These electrodes are electrically connected to the circuitry of a pacemaker to form a leadless Subcutaneous Electrode Array (SEA) for the purpose of detecting cardiac depolarization waveforms displayable as electrocardiographic tracings on a Programmer screen when the programming head is positioned above an implanted pacemaker (or other implanted device) so equipped with a leadless SEA.

This invention is designed to replace existing externally mounted electrodes and electrode wires currently used on the leadless ECG implantable pacemaker, as described in U.S. Pat. No. 5,331,966 issued to Bennett. This previous art had electrodes placed on the face of the implanted pacemaker. When facing muscle, the electrodes were apt to detect myopotentials and were susceptible to baseline drift. The present invention minimizes myopotentials and allows the device to be implanted on either side of the chest by providing maximum electrode separation and minimal signal variation due to various pacemaker orientations within the pocket because the electrodes are placed on the perimeter of the pacemaker in such a way as to maximize the distance between electrode pairs.

The invention will eliminate the need for a compliant shroud that houses surface mounted electrodes and connecting wires as described in patent application Ser. No. 09/697, 438, filed Oct. 26, 2000, entitled Surround Shroud Connector And Electrode Housings For A Subcutaneous Electrode Array And Leadless ECGs, by Ceballos et al. The present invention will also eliminate the need for separate electrodes attached to a feedthrough with their associated assemblies such as those described in P-8786 Multilayer Ceramic Electrodes For Sensing Cardiac Depolarization Signals by Guck et al, and patent application Ser. No. 09/697,438, filed Oct. 26, 2000, entitled Subcutaneous Sensing Feedthrough/ Electrode Assembly by Fraley, et al. Because the thin film electrode is applied to a feedthrough and is a complete functional component with its own hermetically attached weld ring, the assembly can be welded directly into the IPG casing. The use of this invention and the accompanying manufacturing process will eliminate the need for a compliant shroud as well as an attached, separately manufactured electrode. As a result, the manufacturing process will be easier to accomplish and be less expensive. In addition, the present invention provides improvements in the size and handling of the implantable pacemaker during the implant procedure.

The spacing of the electrodes in the present invention provides maximal electrode spacing and, at the same time, appropriate insulation from the pacemaker casing due to the insulative properties of the welding rings into which the electrodes are placed. The electrode spacing around the pacemaker's perimeter maintains a maximum and equal distance between the electrode pairs, in either the three or four preferred electrode configuration as described in patent application Ser. No. 09/697,438.

As in the use of the compliant shroud disclosed in patent application Ser. No. 09/697,438 and helical electrode disclosed in patent application Ser. No. 09/703,152, the present invention also allows the physician or medical technician to perform leadless follow-up that, in turn, eliminates the time it takes to attach external leads to the patient. Such time-savings can reduce the cost of follow-up, as well as making it possible for the physician or medical technician to see more patients during each day. Though not limited to these, other uses include: Holter monitoring with event storage, arrhythmia detection and monitoring, capture detection, ischemia detection and monitoring (S-T elevation and suppression on the ECG), changes in QT interval, and transtelephonic monitoring.

DETAILED DESCRIPTION OF THE DRAWINGS

Figure 1:
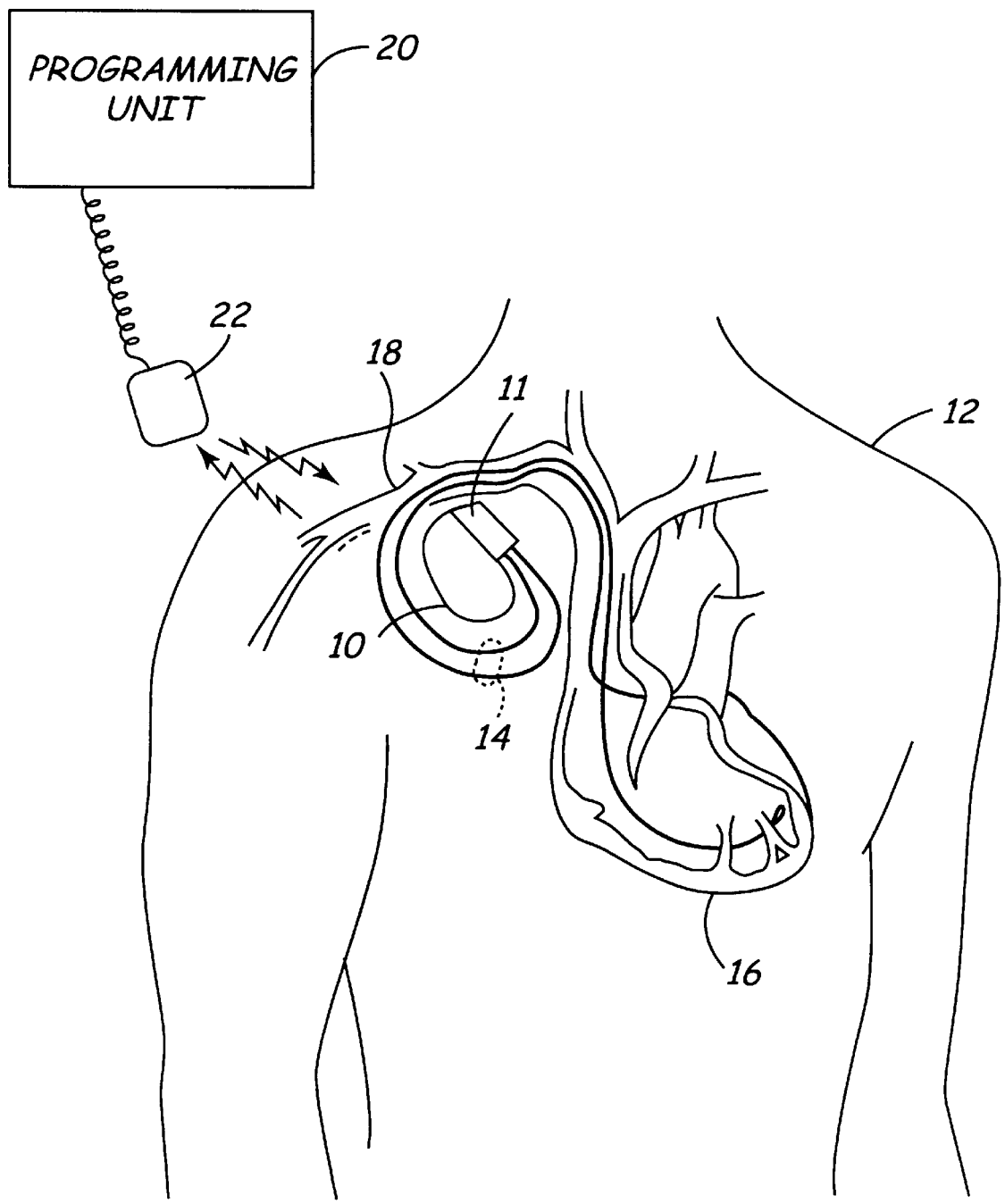
FIG. 1 is an illustration of a body-implantable device system in accordance with the present invention, including a hermetically sealed device implanted in a patient and an external programming unit.

FIG. 1 is an illustration of an implantable medical device system adapted for use in accordance with the present invention. The medical device system shown in FIG. 1 includes an implantable device 10—a pacemaker in this embodiment—that has been implanted in a patient 12. In accordance with conventional practice in the art, pacemaker 10 is housed within a hermetically sealed, biologically inert outer casing, which may itself be conductive so as to serve as an indifferent electrode in the pacemaker's pacing/sensing circuit. One or more pacemaker leads, collectively identified with reference numeral 14 in FIG. 1 are electrically coupled to pacemaker 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, leads 14 may be implanted with its distal end situated in the atrium and/or ventricle of heart 16.

Although the present invention will be described herein in one embodiment which includes a pacemaker, those of ordinary skill in the art having the benefit of the present disclosure will appreciate that the present invention may be advantageously practiced in connection with numerous other types of implantable medical device systems, and indeed in any application in which it is desirable to provide a communication link between two physically separated components.

Also depicted in FIG. 1 is an external programming unit 20 for non-invasive communication with implanted device 10 via uplink and downlink communication channels, to be hereinafter described in further detail. Associated with programming unit 20 is a programming head 22, in accordance with conventional medical device programming systems, for facilitating two-way communication between implanted device 10 and programmer 20. In many known implantable device systems, a programming head such as that depicted in FIG. 1 is positioned on the patient's body over the implant site of the device (usually within 2- to 3-inches of skin contact), such that one or more antennae within the head can send RF signals to, and receive RF signals from, an antenna disposed within the hermetic enclosure of the implanted device or disposed within the connector block of the device, in accordance with common practice in the art.

Figure 2:
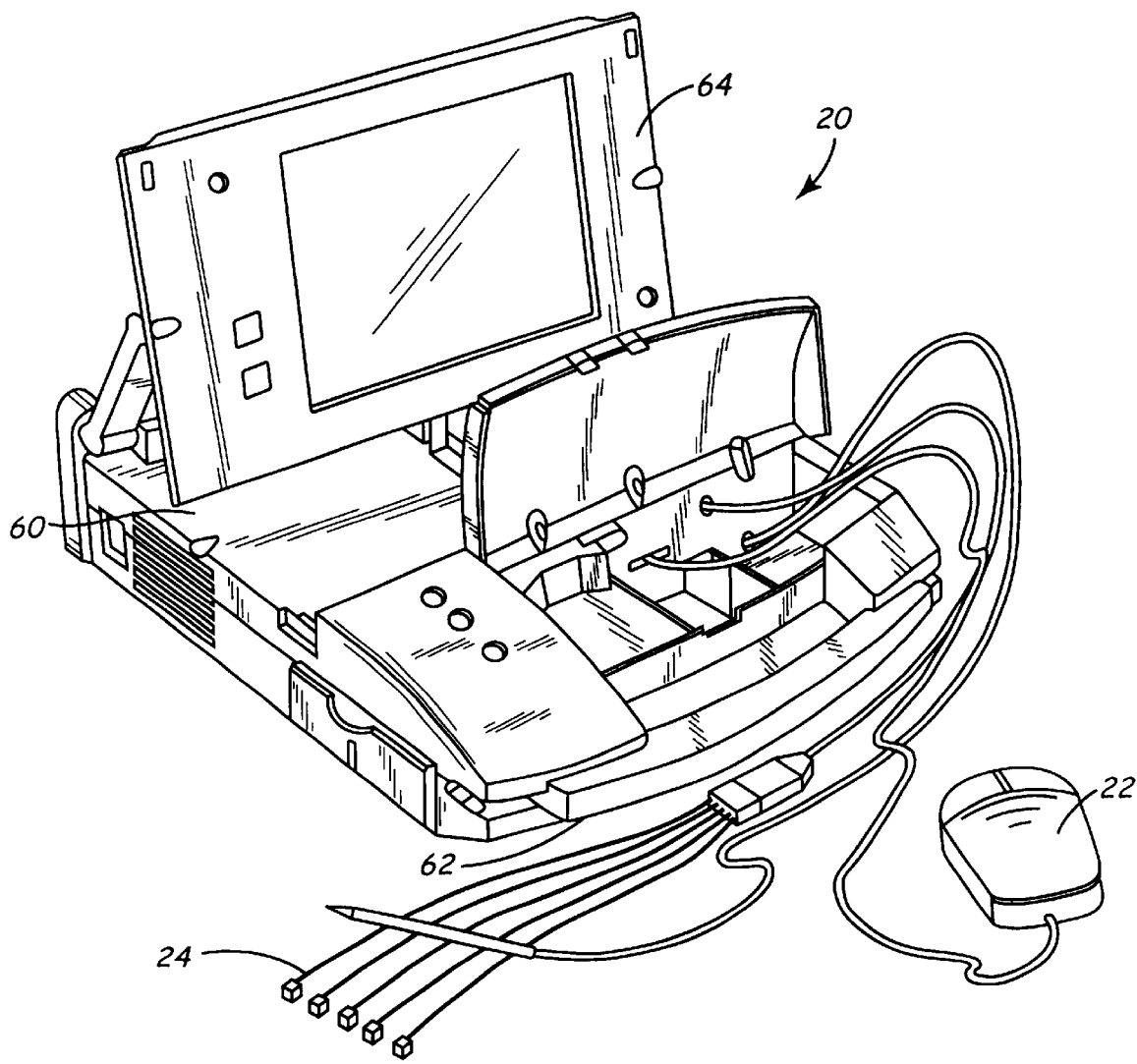
FIG. 2 is a perspective view of the external programming unit of FIG. 1.

FIG. 2 is a perspective view of programming unit 20 in accordance with the presently disclosed invention. Internally, programmer 20 includes a processing unit (not shown in the Figure) that in accordance with the presently disclosed invention is a personal computer type motherboard, e.g., a computer motherboard including an Intel Pentium 3 microprocessor and related circuitry such as digital memory. The details of design and operation of the programmer's computer system will not be set forth in detail in the present disclosure, as it is believed that such details are well-known to those of ordinary skill in the art.

Referring again to FIG. 2, programmer 20 comprises an outer housing 60, which is preferably made of thermal plastic or another suitably rugged yet relatively lightweight material. A carrying handle, designated generally as 62 in FIG. 2, is integrally formed into the front of housing 60. With handle 62, programmer 20 can be carried like a briefcase.

An articulating display screen 64 is disposed on the upper surface of housing 60. Display screen 64 folds down into a closed position (not shown) when programmer 20 is not in use, thereby reducing the size of programmer 20 and protecting the display surface of display 64 during transportation and storage thereof.

A floppy disk drive is disposed within housing 60 and is accessible via a disk insertion slot (not shown). A hard disk drive is also disposed within housing 60, and it is contemplated that a hard disk drive activity indicator, (e.g., an LED, not shown) could be provided to give a visible indication of hard disk activation.

As would be appreciated by those of ordinary skill in the art, it is often desirable to provide a means for determining the status of the patient's conduction system. Normally, programmer 20 is equipped with external ECG leads 24. It is these leads that are rendered redundant by the present invention.

In accordance with the present invention, programmer 20 is equipped with an internal printer (not shown) so that a hard copy of a patient's ECG or of graphics displayed on the programmer's display screen 64 can be generated. Several types of printers, such as the AR-100 printer available from General Scanning Co., are known and commercially available.

In the perspective view of FIG. 2, programmer 20 is shown with articulating display screen 64 having been lifted up into one of a plurality of possible open positions such that the display area thereof is visible to a user situated in front of programmer 20. Articulating display screen is preferably of the LCD or electro-luminescent type, characterized by being relatively thin as compared, for example, a cathode ray tube (CRT) or the like.

As would be appreciated by those of ordinary skill in the art, display screen 64 is operatively coupled to the computer circuitry disposed within housing 60 and is adapted to provide a visual display of graphics and/or data under control of the internal computer.

Programmer 20 described herein with reference to FIG. 2 is described in more detail in U.S. Pat. No. 5,345,362 issued to Thomas J. Winkler, entitled "Portable Computer Apparatus With Articulating Display Panel," which patent is hereby incorporated herein by reference in its entirety. The Medtronic Model 9790 programmer is the implantable device-programming unit with which the present invention may be advantageously practiced.

Figure 3:
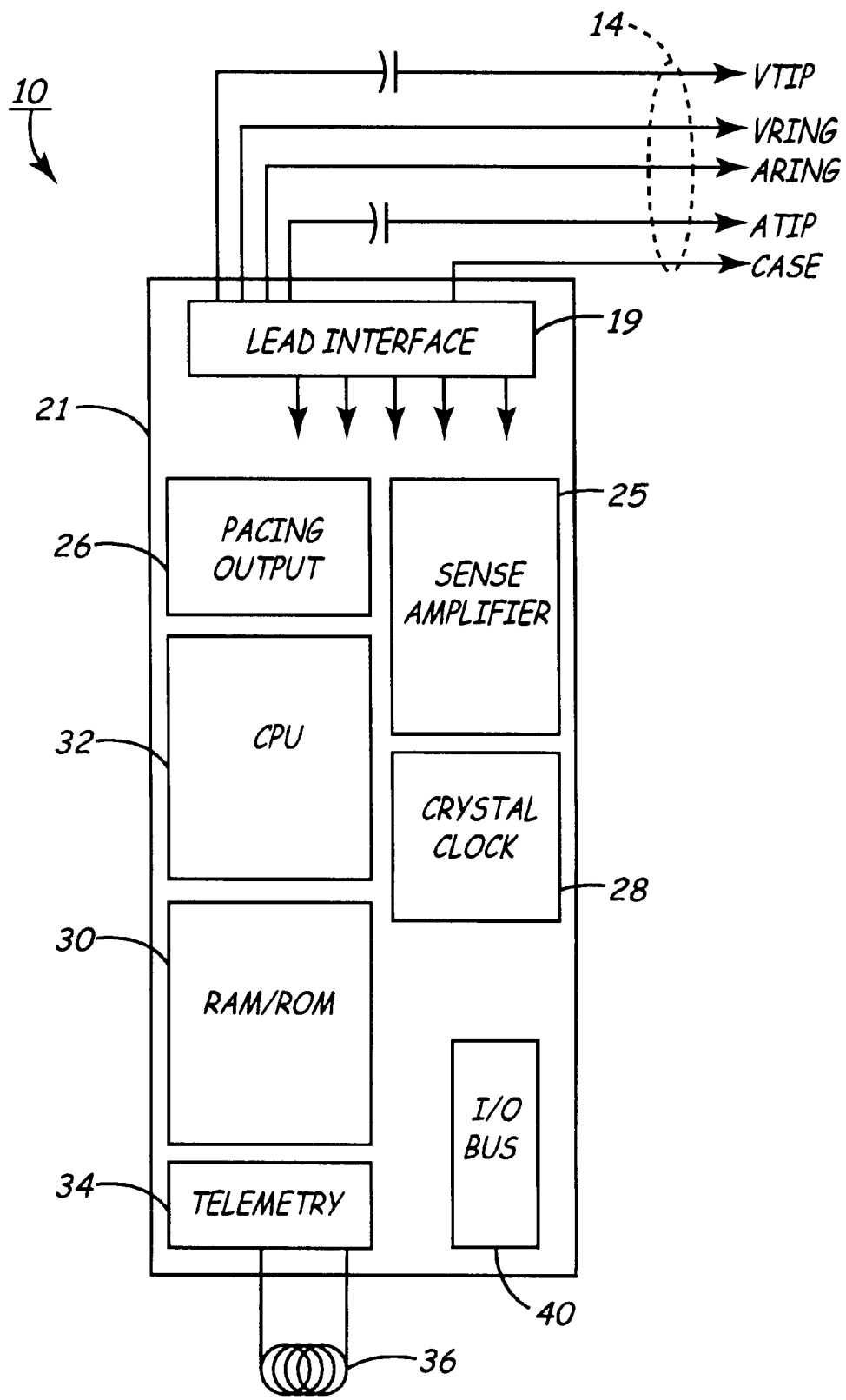
FIG. 3 is a block diagram of the implanted device from FIG. 1.

FIG. 3 is a block diagram of the electronic circuitry that makes up pulse generator 10 in accordance with the presently disclosed invention. As can be seen from FIG. 3, pacemaker 10 comprises a primary stimulation control circuit 21 for controlling the device's pacing and sensing functions. The circuitry associated with stimulation control circuit 21 may be of conventional design, in accordance, for example, with what is disclosed U.S. Pat. No. 5,052,388 issued to Sivula et al., "Method and apparatus for implementing activity sensing in a pulse generator." To the extent that certain components of pulse generator 10 are conventional in their design and operation, such components will not be described herein in detail, as it is believed that design and implementation of such components would be a matter of routine to those of ordinary skill in the art. For example, stimulation control circuit 21 in FIG. 3 includes sense amplifier circuitry 25, stimulating pulse output circuitry 26, a crystal clock 28, a random-access memory and read-only memory (RAM/ROM) unit 30, and a central processing unit (CPU) 32, all of which are well-known in the art.

Pacemaker 10 also includes internal communication circuit 34 so that it is capable communicating with external programmer/control unit 20, as described in FIG. 2 in greater detail.

With continued reference to FIG. 3, pulse generator 10 is coupled to one or more leads 14 which, when implanted, extend transvenously between the implant site of pulse generator 10 and the patient's heart 16, as previously noted with reference to FIG. 1. Physically, the connections between leads 14 and the various internal components of pulse generator 10 are facilitated by means of a conventional connector block assembly 11, shown in FIG. 1. Electrically, the coupling of the conductors of leads and internal electrical components of pulse generator 10 may be facilitated by means of a lead interface circuit 19 which functions, in a multiplexer-like manner, to selectively and dynamically establish necessary connections between various conductors in leads 14, including, for example, atrial tip and ring electrode conductors ATIP and ARING and ventricular tip and ring electrode conductors VTIP and VRING, and individual electrical components of pulse generator 10, as would be familiar to those of ordinary skill in the art. For the sake of clarity, the specific connections between leads 14 and the various components of pulse generator 10 are not shown in FIG. 3, although it will be clear to those of ordinary skill in the art that, for example, leads 14 will necessarily be coupled, either directly or indirectly, to sense amplifier circuitry 24 and stimulating pulse output circuit 26, in accordance with common practice, such that cardiac electrical signals may be conveyed to sensing circuitry 24, and such that stimulating pulses may be delivered to cardiac tissue, via leads 14. Also not shown in FIG. 3 is the protection circuitry commonly included in implanted devices to protect, for example, the sensing circuitry of the device from high voltage stimulating pulses.

As previously noted, stimulation control circuit 20 includes central processing unit 32 which may be an off-the-shelf programmable microprocessor or micro controller, but in the present invention is a custom integrated circuit. Although specific connections between CPU 32 and other components of stimulation control circuit 20 are not shown in FIG. 3, it will be apparent to those of ordinary skill in the art that CPU 32 functions to control the timed operation of stimulating pulse output circuit 26 and sense amplifier circuit 24 under control of programming stored in RAM/ROM unit 30. It is believed that those of ordinary skill in the art will be familiar with such an operative arrangement.

With continued reference to FIG. 3, crystal oscillator circuit 28, in the presently preferred embodiment a 32,768-Hz crystal controlled oscillator provides main timing clock signals to stimulation control circuit 20. Again, the lines over which such clocking signals are provided to the various timed components of pulse generator 10 (e.g., microprocessor 32) are omitted from FIG. 3 for the sake of clarity.

It is to be understood that the various components of pulse generator 10 depicted in FIG. 3 are powered by means of a battery (not shown) which is contained within the hermetic enclosure of pacemaker 10, in accordance with common practice in the art. For the sake of clarity in the Figures, the battery and the connections between it and the other components of pulse generator 10 are not shown.

Stimulating pulse output circuit 26, which functions to generate cardiac stimuli under control of signals issued by CPU 32, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits that would be suitable for the purposes of practicing the present invention.

Sense amplifier circuit 24, which is of conventional design, functions to receive electrical cardiac signals from leads 14 and to process such signals to derive event signals reflecting the occurrence of specific cardiac electrical events, including atrial contractions (P-waves) and ventricular contractions (R-waves). CPU provides these event-indicating signals to CPU 32 for use in controlling the synchronous stimulating operations of pulse generator 10 in accordance with common practice in the art. In addition, these event-indicating signals may be communicated, via uplink transmission, to external programming unit 20 for visual display to a physician or clinician.

Those of ordinary skill in the art will appreciate that pacemaker 10 may include numerous other components and subsystems, for example, activity sensors and associated circuitry. The presence or absence of such additional components in pacemaker 10, however, is not believed to be pertinent to the present invention, which relates primarily to the implementation and operation of communication subsystem 34 in pacemaker 10, and an associated communication subsystem in external unit 20.

Figure 4:
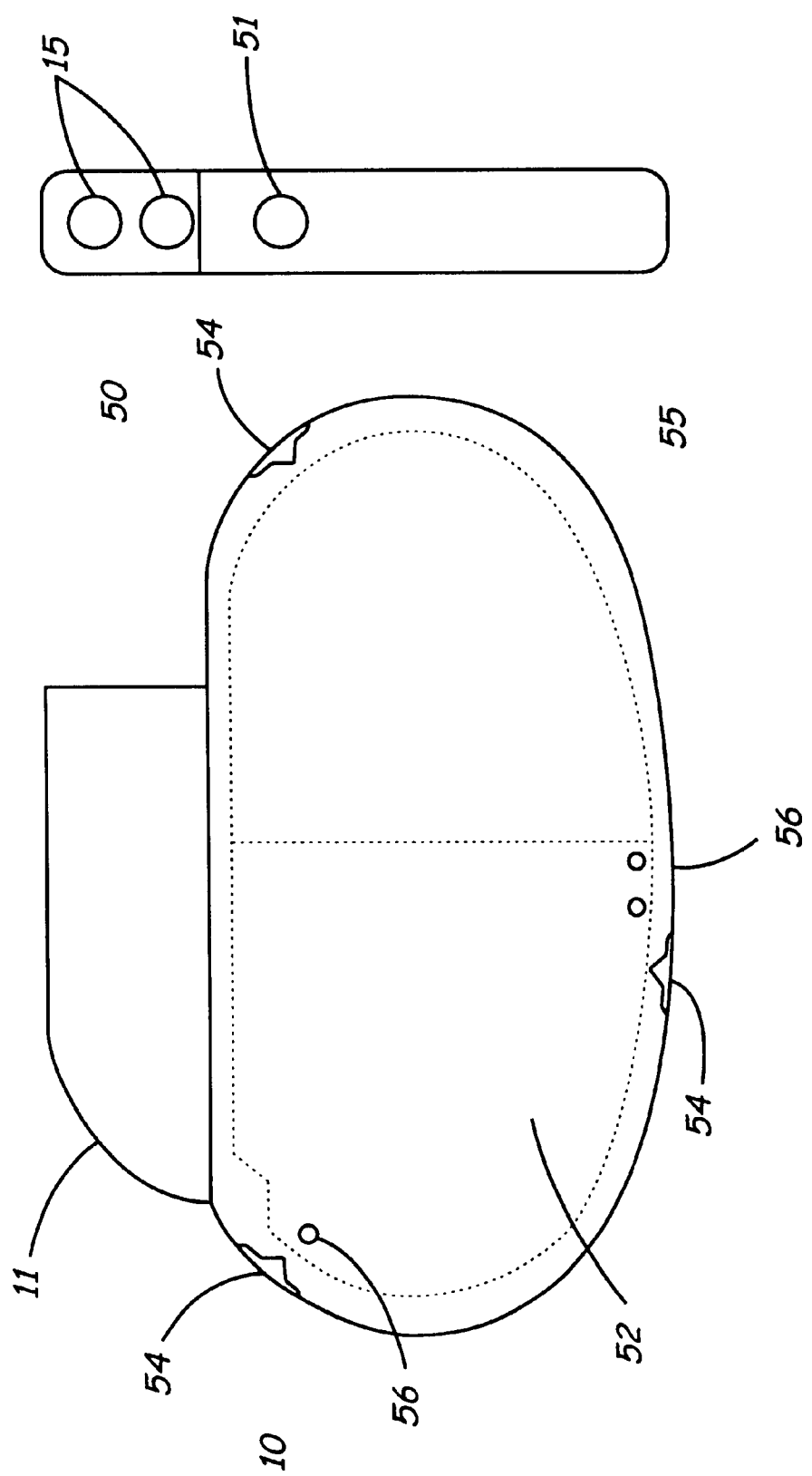
FIG. 4 is a cross sectional view of an implanted pacemaker in which the present invention may be practiced as a preferred embodiment.

FIG. 4 is a cross sectional view of implanted pacemaker 10 in which the present invention may be practiced as the preferred embodiment. The major components of pacemaker 10 consist of a hermetic casing in which are housed electronic circuitry 52 and a hermetic power source 50, in this case, a lithium-iodine battery. Lead connector module 11 provides an enclosure into which proximal ends of atrial and ventricular leads may be inserted into openings 15. Lead connector module is connected to pacemaker casing 10 and has electrical connections (not shown) between lead connectors and hermetic feedthroughs (also not shown).

Continuing with FIG. 4, thin film electrodes 51 are welded into place on the flattened periphery of the pacemaker casing. In this preferred embodiment, the complete periphery of the pacemaker may be manufactured to have a slightly flattened perspective with rounded edges to accommodate the placement of electrodes such as those practiced in the present invention. Thin film electrode feedthroughs 54 are welded to pacemaker casing (to preserve hermeticity) and are connected via wire 55 through feedthroughs 56 to electronic circuitry 52.

Figure 5:
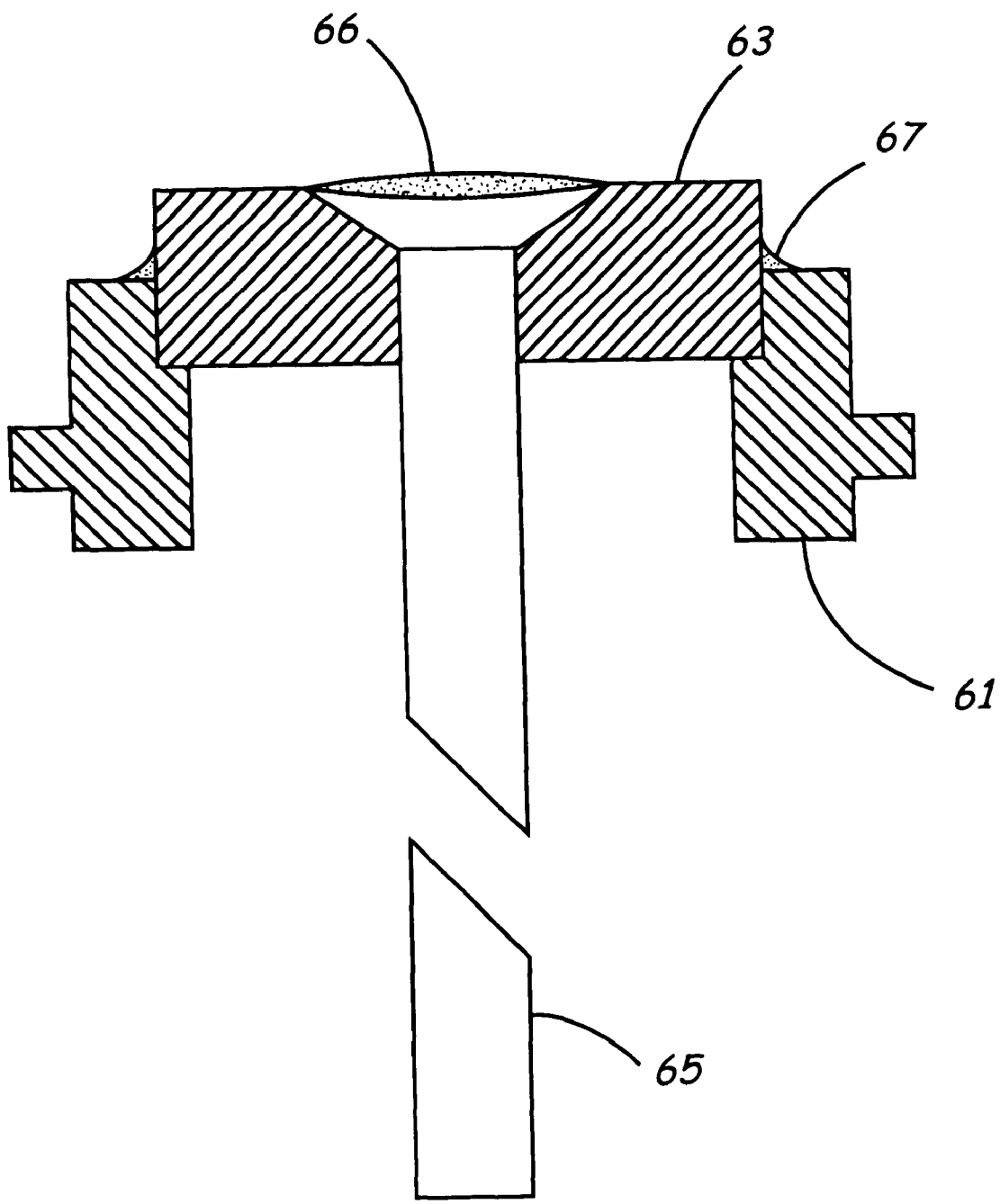
FIG. 5 is a cross sectional view of the feedthrough pin within the assembly prior to fabrication and application of thin film electrode.

FIG. 5 is a cross sectional view of standard feedthrough head 66 and pin 65, mounted in assembly consisting of ferrule 61 and insulation 63. The device is an industry standard terminal feedthrough used widely in other Medtronic products. Ferrule 61 is welded to insulation 63 by brazing 67. The ferrule may be constructed of titanium or other such material. The insulator may be a single crystal sapphire or a polycrystalline aluminum oxide. Braze materials include gold, gold alloys, and niobium alloys. Feedthrough head 66 comes equipped with a conductive metal such as gold braze. As used in previous art, feedthrough head 66 would be in contact with a separate electrode to detect changes in electrical potentials (cardiac depolarization waves). In such an application, the signal from the electrode would necessarily require a conductive metal on feedthrough head 66 to ensure transfer of the signal to the pacemaker's electronic circuitry. The present invention takes a novel approach in that the feedthrough head will itself become the sensing electrode, thus eliminating the need for a separate electrode.

Figure 6:
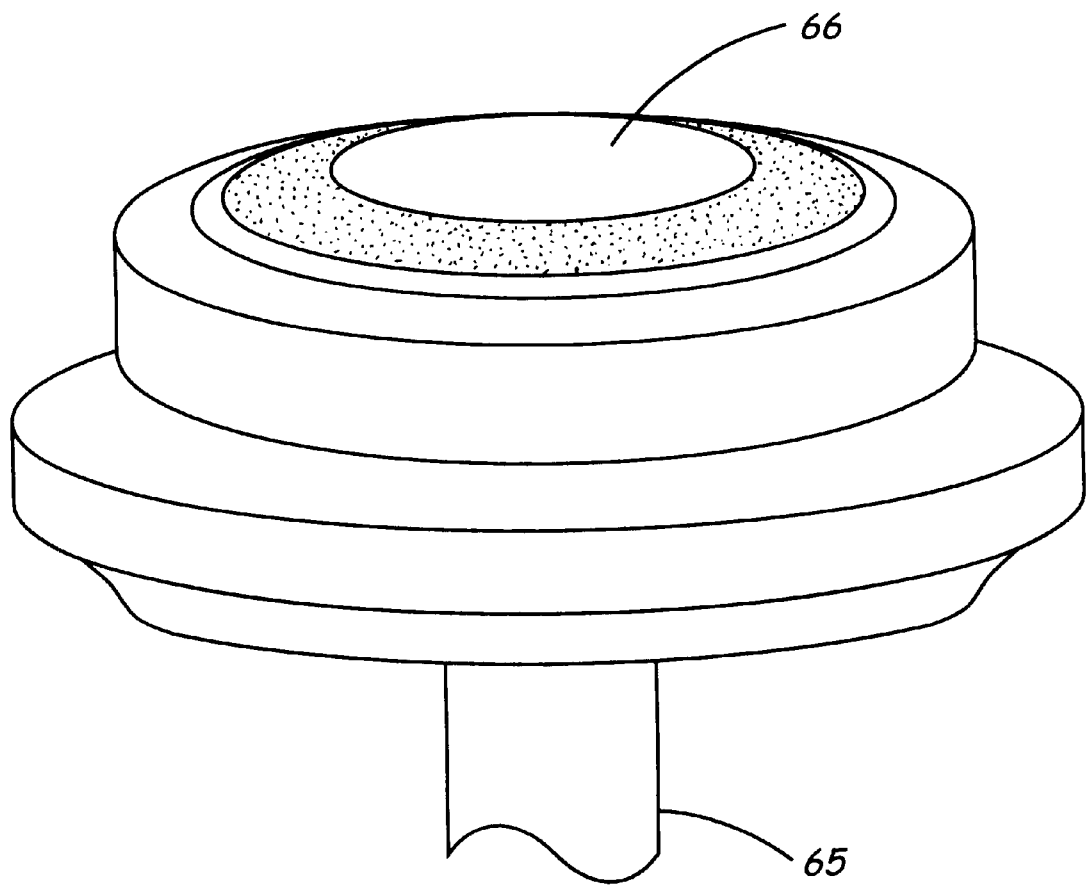
FIG. 6 is a perspective view of polished head of feedthrough pin prior to application of thin film electrode.

FIG. 6 is a perspective view of polished feedthrough head 66 prior to application of thin film electrode. Feedthrough head 66 is modified in the manufacturing process. The surface is ground and polished prior to thin film deposition. The first step in this process is to grind away the conductive metal with which the feedthrough head is equipped (shown in FIG. 5). After grinding, the surface of the feedthrough head is polished 65.

Figure 7:
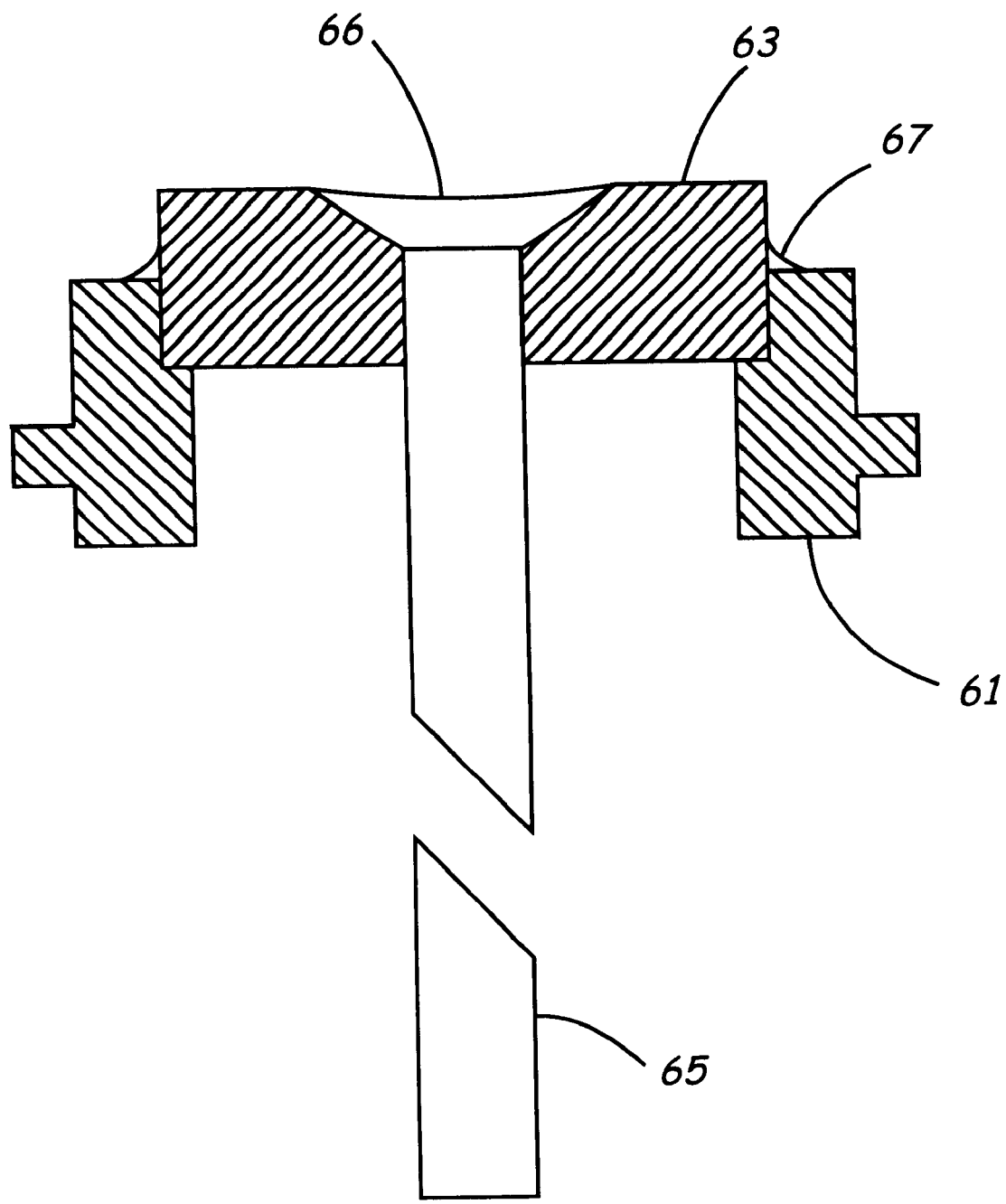
FIG. 7 is a cross sectional view of polished head of feedthrough pin prior to application of thin film electrode.

FIG. 7 is a cross sectional view of polished feedthrough head 66 prior to deposition of the thin film electrode. During the grinding and polishing process, the feedthrough head will become slightly indented as shown in this figure. Electrode deposition may consist of a wide variety of materials or by laser beam metalization coating techniques or spray techniques. Various metals and metal alloys can be used for the electrode surface and are readily testable, including titanium nitride, iridium oxide, platinum, gold, and so on.

Figure 8:
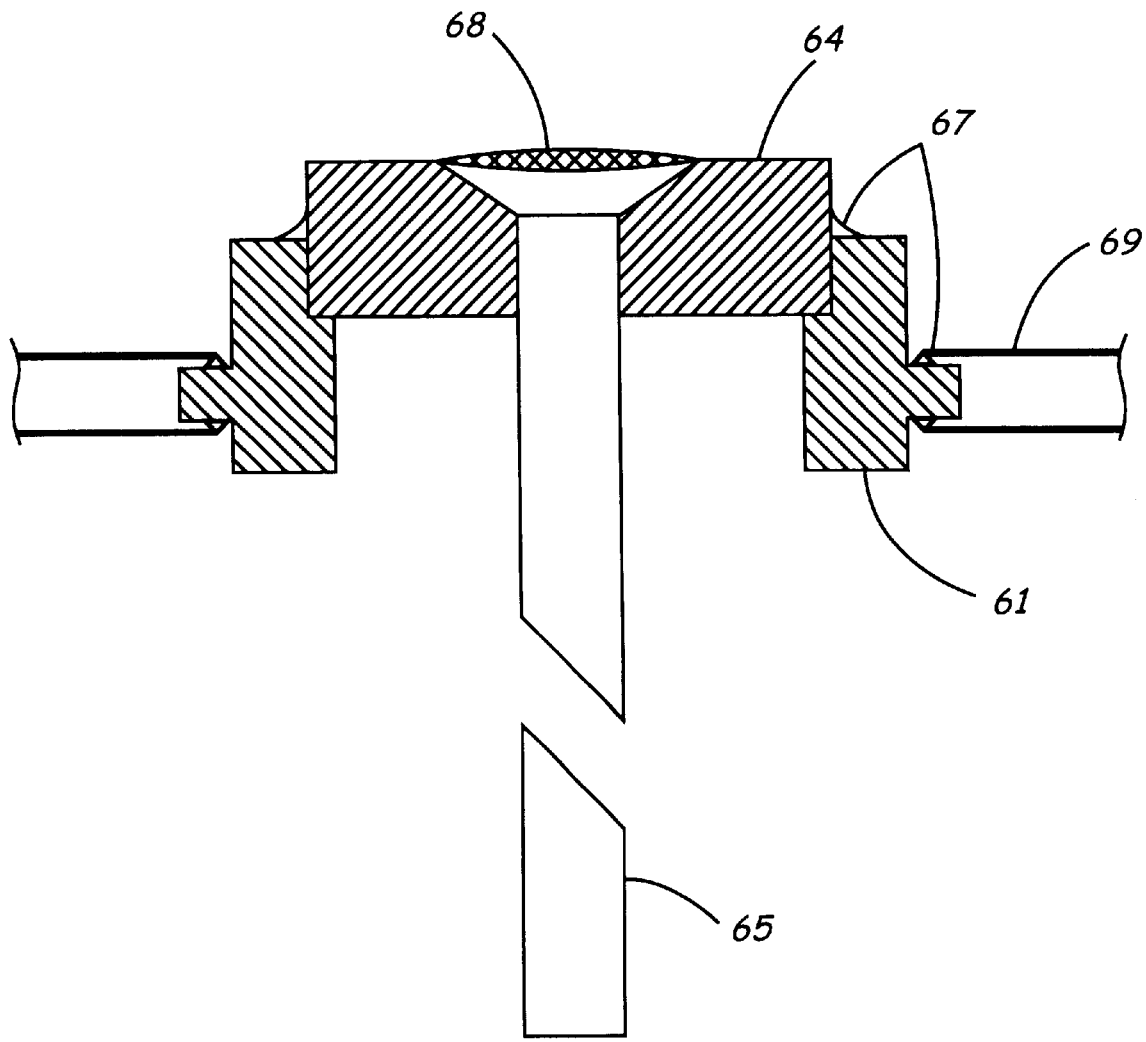
FIG. 8 is a cross sectional view of feedthrough pin after application of thin film electrode.

FIG. 8 is a cross sectional view of feedthrough head and pin after application of thin film electrode 68. Thin film electrode 68 has an underlying adhesion layer (not shown) to ensure stability of the electrode. The electrode is then tested for adhesion, hermeticity, electrical performance, and thin film integrity. The thin film electrode is then tested and compared to previous specifications established for other types of electrodes established by impedance and capacitance spectroscopy, that is, to determine whether the signal sensing is appropriate over a determined range of frequencies. The finished and tested feedthrough is mounted in insulator 61 via brazing 67, and then attached to pacemaker casing 69 via brazing 67.

The manufacturing steps and testing processes are much simplified when compared to those required for other electrodes such as described in patent application Ser. Nos. 09/697,438, 09/703,152 and 09/696,365 hereinabove. The use of a modified feedthrough with thin film deposition should result in cost savings that, in turn, can be passed on to the medical community and insurers.

What is claimed is:

1. A data collection system implemented with a medical device for recording electrocardiographic data, the system comprising:
    an hermetically sealed case; and
    an array of subcutaneous thin film electrodes mounted on a surface of a feedthrough; and
    signal processing circuitry inside the case coupled with the electrodes via the feedthrough.

2. The system of claim 1 wherein the electrodes are mounted on the surface of said feedthrough by thin film deposition and wherein the surface of the feedthrough is polished and ground prior to deposition of the thin film electrodes.

3. The system of claim 2 wherein the case includes walls into which body fluid is allowed to flow so that the body fluid is above and around the thin film electrodes, and is mounted on the surface of said feedthrough.

4. The system of claim 1 wherein said feedthrough includes a head and a pin assembly further comprising a ferrule and insulation.

5. The system of claim 4 wherein said ferrule is made from material selected from the group consisting of titanium, titanium 64, niobium, titanium/niobium alloy, stainless steel and equivalent laser weldable and brazeable alloys.

6. The system of claim 5 wherein said insulator is one of a single crystal sapphire and a polycrystalline aluminum oxide.

7. The system of claim 1 wherein said feedthrough includes a head having a conductive metal selected from the group of materials consisting of gold, gold alloys and niobium alloys, and equivalent metal alloys.

8. The system of claim 1 wherein said thin film electrode includes a sensing electrode attached to the feedthrough surface.

9. A method of attaching a thin film electrode to a hermetically sealed case, the method comprising:
    forming a slightly flattened area on a perimeter surface of a hermetically sealed case; and
    depositing the thin film electrode on a feedthrough; and
    welding the feedthrough to the slightly flattened area on the perimeter surface of the case.

10. The method of claim 9 wherein said feedthrough includes a head and the thin film is deposited after grinding and polishing the head.

11. The method of claim 10 wherein said head is slightly indented after the grinding and polishing method.

12. The method of claim 9 wherein the thin film electrode is deposited including one of laser beam a metalization coating and spray techniques.

13. The method of claim 9 wherein the thin film electrode includes an underlying adhesion layer to ensure stabilizing the electrode and hermeticity.

14. A data collection system implemented with a medical device for recording electrocardiographic data including a thin film electrode scheme distributed about the perimeter of a hermetically sealed case, the electrode scheme in combination, comprising:
    a hermetically sealed case; and
    a plurality of subcutaneous thin film electrodes forming a distributed array spaced apart to optimally cover and receive signals from all directions and connected to signal processing circuitry inside the case coupled with the electrode via a feedthrough assembly in operable electrical contact with amplifiers in a microprocessor circuitry.

15. The thin film electrode scheme of claim 14 wherein one of three and four electrodes form the array in said spaced-apart relations therewith.

* * * * *